United States Patent [19]

Hall et al.

[11] Patent Number: 4,845,130

[45] Date of Patent: Jul. 4, 1989

[54] ANTIHYPERLIPIDEMIC AMINES

[75] Inventors: Iris H. Hall, Chapel Hill, N.C.; Thomas S. Griffin, Trabuco Canyon; Edward L. Docks, Orange, both of Calif.

[73] Assignee: United States Borax & Chemical Corporation, Los Angeles, Calif.

[21] Appl. No.: 182,689

[22] Filed: Apr. 18, 1988

[51] Int. Cl.⁴ ............................................. A61K 31/13
[52] U.S. Cl. .................................... 514/663; 514/824
[58] Field of Search .............................. 514/663, 824

[56] References Cited

FOREIGN PATENT DOCUMENTS 673277 10/1963 Canada ................................. 514/663

Primary Examiner—Douglas W. Robinson
Assistant Examiner—Raymond J. Henley, III
Attorney, Agent, or Firm—James R. Thornton

[57] ABSTRACT

Long chain alkyl amines are useful as anti-hyperlipidemic agents for lowering serum cholesterol and triglyceride levels in mammals. Such amines include compounds of the formula

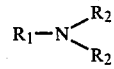

in which $R_1$ is alkyl of 8 to 20 carbon atoms and each $R_2$ is hydrogen or alkyl of 1 to 3 carbon atoms.

11 Claims, No Drawings

ANTIHYPERLIPIDEMIC AMINES

SUMMARY OF THE INVENTION

This invention relates to the use of certain long chain aliphatic amines as antihyperlipidemic or hypolipidemic agents to control mammalian diseases associated with increased serum cholesterol or triglyceride levels.

RELATED PATENTS AND APPLICATIONS

Co-pending U.S. application Ser. No. 011,178 filed Feb. 5, 1987 by Iris H. Hall, R. J. Brotherton and E. L. Docks, now U.S. Pat. No. 4,740,504, describes the use of certain long chain alkyl amine boranes as antihyperlipidemic agents. The entire disclosure thereof is incorporated herein by reference. See also Hall, "Abstracts, 36th Southeastern Regional Meeting American Chemical Society", Oct. 24–26, 1984, Abstract No. 332 and Hall et al., Journal of Pharmaceutical Sciences, Vol. 75, No. 7, July 1986, Pages 706–710.

Iris H. Hall et al. U.S. Pat. No. 4,672,060, dated June 9, 1987, describes the use of certain ammonium salts of polyboranes as antihyperlipidemic agents.

BACKGROUND OF THE INVENTION

Hall et al., J. Pharm. Sci. 70, 339–341 (1981) reported that a series of trimethylamine cyanoboranes and trimethylamine carboxyboranes possess potent hyperlipidemic activity at a dose of 5–20 mg/kg/day. These derivatives lowered serum cholesterol levels, reportedly due to the agents' ability to suppress HMG CoA reductase activity. Reduction of serum triglyceride levels was correlated with the inhibition of fatty acid synthetase by the agents. Subsequently, Hall et al., J. Pharm. Sci. 73, 973–977 (1984) reported that tetrakis-u-(trimethylamine-borane carboxyato) bis(trimethylaminecarboxyborane)-dicopper (II) was observed to be a potent hypolipidemic agent at the low dose of 2.5 mg/kg in mice. The dicopper complex was observed to lower ATP dependent citrate lyase, acetyl CoA synthetase and phosphatidate phosphohydrolase in vivo and to accelerate cholesterol excretion from the body.

Certain amine borane derivatives which are described as boron analogs of α-amino acids have been patented as anti-inflammatory agents. See Spielvogel et al. U.S. Pat. No. 4,312,989 issued Jan. 26, 1982.

DESCRIPTION OF THE INVENTION

It has been found that long chain aliphatic amines are potent hypolipidemic agents which are effective in decreasing the serum cholesterol and triglyceride levels in mammals.

The aliphatic amines of the present invention are the long chain alkyl amines which can be defined as having the general formula:

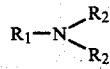

in which $R_1$ represents alkyl having from about 8 to about 20 carbon atoms and $R_2$ represents hydrogen or alkyl of 1 to about 3 carbon atoms.

The long chain alkyl amines are well known and are readily prepared by known procedures. Typical examples include decylamine, undecylamine, octylamine, octadecylamine, dodecylamine, N-methyloctadecylamine, N-ethyl-dodecylamine, N,N-dimethyl-n-octadecylamine, N,N-dimethyl-decylamine, and the like. The primary amines are preferred, especially those having straight chain alkyl groups.

The alkyl amines of this invention are effective antihyperlipidemic agents, being effective both after intraparenteral and oral administration. They have been found to significantly decrease serum cholesterol and serum triglycerides in mice. When the compounds are employed as hypolipidemic agents, they can be administered to warm-blooded mammals such as mice, rats, rabbits, dogs, cats, mokeys, etc. alone or in combination with pharmacologically acceptable carriers, the proportion of which is determined by the solubility and chemical nature of the compounds, the chosen route of administration and standard biological practice. For example, they may be administered orally in the form of tablets, capsules, lozenges, and the like containing extenders such as starch, milk, sugar, etc. They may also be administered orally in the form of solutions or they may be injected parenterally. For parenteral administeration they may be used in the form of sterile solutions containing other solutes, for example, enough saline or glucose to make the solution isotonic.

The dosage of the compounds will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects, such as at a level that is in the range of from about 4 mg. to about 40 mg. per kilo per day, although as mentioned above, variations will occur. Preferably, about 8 to 20 mg. per kilo per day is adminstered.

EXAMPLE 1

For determining hypolipidemic activity, representative compounds of this invention were suspended in an aqueous 1% carboxymethylcellulose solution and tested at 20 mg./kg./ day administered intraparenterally to male $CF_1$ mice (~25 g.). Six animals were used for each test. On days 9 and 16, blood was collected by tail vein bleeding and the serum separated by centrifugation for three minutes. Serum cholesterol levels were determined by a modified Liebermann-Burchard reaction. Serum triglyceride levels were also determined at 16 days using a Fisher-Hycel Triglyceride Test Kit. The results are presented in the following Table.

|  | % of Control | | |
| --- | --- | --- | --- |
|  | Serum Cholesterol | | Serum Triglyceride |
| Compound | Day 9 | Day 16 | Day 16 |
| N—methyloctadecylamine | 51 ± 5 | 44 ± 4 | 64 ± 6 |
| decylamine | 48 ± 4 | 38 ± 5 | 59 ± 6 |
| undecylamine | 61 ± 5 | 57 ± 6 | 66 ± 5 |
| dodecylamine | 63 ± 6 | 61 ± 5 | 64 ± 4 |
| tridecylamine | 69 ± 5 | 67 ± 5 | 73 ± 7 |
| 1-tetradecylamine | 50 ± 4 | 34 ± 3 | 54 ± 6 |
| 1-hexadecylamine | 39 ± 5 | 35 ± 4 | 63 ± 6 |
| octadecylamine | 72 ± 5 | 64 ± 4 | 56 ± 4 |
| N,N—dimethyl-n-octadecylamine | 76 ± 6 | 61 ± 5 | 56 ± 3 |
| clofibrate (150 mg.)* | 88 ± 7 | 87 ± 5 | 75 ± 5 |

-continued

| | % of Control | | |
|---|---|---|---|
| | Serum Cholesterol | | Serum Triglyceride |
| Compound | Day 9 | Day 16 | Day 16 |
| 1% CMC | 100 | 100 | 100 |

*clofibrate, a commercially available drug, was tested at its therapeutic dose of 150 mg.

EXAMPLE 2

The procedure of Example 1 was repeated with octade-cylamine and N,N-dimethyl-n-octadecylamine at a dosage of 8 mg./kg/ day. The results were as follows:

| | % of Control | | |
|---|---|---|---|
| | Serum cholesterol | | Serum Triglyceride |
| | Day 9 | Day 16 | Day 16 |
| octadecylamine | 63 ± 3 | 57 ± 4 | 60 ± 5 |
| N,N—dimethyl-n-octadecylamine | 91 ± 5 | 79 ± 5 | 84 ± 6 |

Various changes and modifications of the invention can be made, and to the extent that such variations incorporate the spirit of this invention, they are intended to be included within the scope of the appended claims.

What is claimed is:

1. A method of decreasing serum cholesterol and triglyceride levels in mammals in need thereof which comprises administering to said mammal a therapeutically effective amount of a long chain alkyl amine having the formula

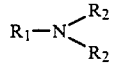

in which $R_1$ is alkyl having from 8 to about 20 carbon atoms and each $R_2$ is hydrogen or alkyl of 1 to 3 carbon atoms.

2. The method according to claim 1 in which each of said $R_2$ is methyl or hydrogen.

3. The method according to claim 2 in which said $R_2$ is hydrogen.

4. The method according to claim 2 in which said long chain alkyl amine is a straight chain primary amine.

5. The method according to claim 2 in which said long chain alkyl amine is octadecylamine.

6. The method according to claim 2 in which said long chain alkyl amine is decylamine.

7. The method according to claim 2 in which said long chain alkyl amine is tetradecylamine.

8. The method according to claim 2 in which said long chain alkyl amine is hexadecylamine.

9. The method according to claim 2 in which said long chain alkyl amine is N-methyloctadecylamine.

10. The method according to claim 2 in which said long chain alkyl amine is administered at a dosage of from about 4 to about 40 mg./kg/day.

11. The method according to claim 2 in which said long chain alkyl amine is administered at a dosage of from about 8 to about 20 mg./kg./day.

* * * * *